(12) United States Patent
Ho

(10) Patent No.: US 7,975,694 B2
(45) Date of Patent: Jul. 12, 2011

(54) NON-INTRUSIVE MASK INTERFACE WITH NASAL SUPPORT

(75) Inventor: Peter Chi Fai Ho, Pittsburgh, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 428 days.

(21) Appl. No.: 12/274,722

(22) Filed: Nov. 20, 2008

(65) Prior Publication Data

US 2009/0120442 A1    May 14, 2009

Related U.S. Application Data

(63) Continuation-in-part of application No. 11/585,320, filed on Oct. 23, 2006, now Pat. No. 7,556,043.

(60) Provisional application No. 60/729,516, filed on Oct. 24, 2005.

(51) Int. Cl.
     *A62B 18/02*      (2006.01)

(52) U.S. Cl. .......... 128/207.13; 128/205.25; 128/206.21

(58) Field of Classification Search ............. 128/205.25, 128/206.12, 206.18, 206.21, 206.27, 206.28, 128/207.12, 207.13

See application file for complete search history.

(56) References Cited

U.S. PATENT DOCUMENTS

| | | | |
|---|---|---|---|
| 4,248,218 A | 2/1981 | Fischer | |
| 4,782,832 A | 11/1988 | Trimble | |
| 4,919,128 A * | 4/1990 | Kopala et al. | 128/207.18 |
| 6,119,694 A | 9/2000 | Correa | |
| 6,192,886 B1 * | 2/2001 | Rudolph | 128/207.13 |
| 6,397,847 B1 * | 6/2002 | Scarberry et al. | 128/206.24 |
| 6,418,928 B1 | 7/2002 | Bordewick | |
| 6,581,601 B2 | 6/2003 | Ziaee | |
| 6,651,663 B2 | 11/2003 | Barnett | |
| 7,156,096 B2 | 1/2007 | Landis | |
| D542,912 S | 5/2007 | Gunaratnam | |
| 7,556,043 B2 * | 7/2009 | Ho et al. | 128/207.18 |
| 7,658,189 B2 * | 2/2010 | Davidson et al. | 128/205.25 |
| 2002/0053347 A1 | 5/2002 | Ziaee | |
| 2002/0096178 A1 | 7/2002 | Ziaee | |
| 2005/0076913 A1 | 4/2005 | Ho | |

* cited by examiner

*Primary Examiner* — Steven O Douglas

(74) *Attorney, Agent, or Firm* — Michael W. Haas

(57) ABSTRACT

A patient interface includes a body member, a partition, a nasal seal portion, and a port. The partition is integral with the body member, and separates an interior of the member into a first chamber configured to receive a nose of a patient and a second chamber. The nasal seal portion is integral with the partition, and projects therefrom into the first chamber. The nasal seal portion includes a seal surface and a gas passage therethrough. The seal surface is configured to conform with a lower portion of the nose that is surrounding nasal passages of the patient, without entering the nasal passages of the patient, when the patient interface is mounted operatively on the face of the patient. The port integral with the member is in fluid communication with the second chamber for delivery of gas to the patient via the gas passage in the nasal seal portion.

21 Claims, 15 Drawing Sheets

NON-INTRUSIVE MASK INTERFACE WITH NASAL SUPPORT

CROSS-REFERENCE TO RELATED APPLICATIONS

Under the provisions of 35 U.S.C. §120/365, this application claims the benefit of U.S. application Ser. No. 11/585,320, filed Oct. 23, 2006, which, under the provisions of 35 U.S.C. §119(e), claims the benefit of U.S. provisional patent application Ser. No. 60/729,516, filed Oct. 24, 2005. The contents of which are hereby incorporated by reference.

BACKGROUND OF THE INVENTION

1. Field of the Invention

The present invention generally relates to a patient interface for use in a pressure support system that supplies a flow of gas to the airway of a patient.

2. Description of Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), Cheyne-Stokes respiration, or congestive heart failure.

Non-invasive ventilation and pressure support therapies involve the placement of a patient interface, which is typically a nasal, nasal/oral mask, or a total face mask, on the face of a patient. The patient interface couples the ventilator or pressure support system with the airway of the patient, so that a flow of breathing gas can be delivered from the flow/pressure generating device to the airway of the patient.

Because patient interfaces are typically worn for an extended period of time, a variety of concerns must be taken into consideration. For example, in providing CPAP to treat OSA, the patient normally wears the patient interface all night long while he or she sleeps. One concern in such a situation is that the patient interface is as comfortable as possible, otherwise the patient may avoid wearing the interface device, defeating the purpose of the prescribed pressure support therapy. It is also desirable for the patient interface to provide an adequate seal against the patient's face without discomfort.

Typically, patient interfaces include a member housing shell and a cushion (also referred to as a seal or seal member) attached to the shell. The cushion contacts the surface of the patient and operates to both locate and seal the interface with the face of the patient. The member is held in place by a headgear assembly that wraps around the head of the patient. Together, the patient interface and headgear form a patient interface assembly. A typical headgear assembly includes flexible, adjustable straps that extend from the patient interface to attach the patient interface to the patient.

The present invention provides improvements over prior art patient interfaces.

SUMMARY OF THE INVENTION

One aspect of the present invention provides a patient interface. The patient interface includes a body member, a partition, a nasal seal portion, and a port. The partition is integral with the body member, and separates an interior of the member into a first chamber configured to receive a nose of a patient and a second chamber. The nasal seal portion is integral with the partition, and projects therefrom into the first chamber. The nasal seal portion includes a seal surface and a gas passage therethrough. The seal surface is configured to conform with a lower portion of the nose that is surrounding nasal passages of the patient, without entering the nasal passages of the patient, when the patient interface is mounted operatively on the face of the patient. The port integral with the member is in fluid communication with the second chamber for delivery of gas to the patient via the gas passage in the nasal seal portion.

Another aspect of the present invention provides a patient interface. The patient interface includes an outer body member, a peripheral outer seal, a nasal seal portion, and a port. The outer body member is formed from a resilient material. The peripheral outer seal is integral with the body member. The outer seal includes peripheral surface regions that are arranged to engage the bridge of a patient's nose and a region above the patient's upper lip. The nasal seal portion is at least partially disposed within the outer body member. The nasal seal portion includes an upper seal surface and a gas passage therethrough. The upper seal surface includes a generally concave configuration as it extends in a left-right direction and arranged to conform with a lower portion of the nose that surrounds that nasal passages of the patient. The upper seal surface is devoid of projections that would enter the nasal passages of the patient. The port is integral with the body member for delivering gas to the patient via the gas passage in the nasal seal portion.

These and other aspects of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. For disclosure purposes, the drawings attached hereto can be to scale as exemplary embodiments. It is to be expressly understood, however, that the drawings are for the purpose of illustration and description only and are not at all intended as a definition of the limits of the invention. As used in the specification and in the claims, the singular form of "a", "an", and "the" include plural referents unless the context clearly dictates otherwise.

DETAILED DESCRIPTION OF THE INVENTION

FIGS. 4-9 show a patient interface 10 for use in a pressure support system (not shown) that supplies a flow of gas to the airway of a patient in accordance with an embodiment of the present invention. The patient interface 10 is configured to communicate a flow of gas between the patient's airway or nasal passages and a pressure generating device (not shown). Numerous pressure generating devices are usable with the interface 10. Non-limiting examples include a ventilator, CPAP device, variable pressure device, in which the pressure provided to the patient varies with the patient's respiratory cycle so that a higher pressure is delivered during inspiration than during expiration, or auto-titration device in which the pressure varies with the condition of the patient, such as whether the patient is snoring, experiencing an apnea, hypopnea, or upper airway resistance. Communicating a flow of breathing gas between the patient's airway and a pressure generating device includes delivering a flow of breathing gas to the patient from the pressure generating device and exhausting a flow of gas from the patient to ambient atmosphere.

Figure 1:
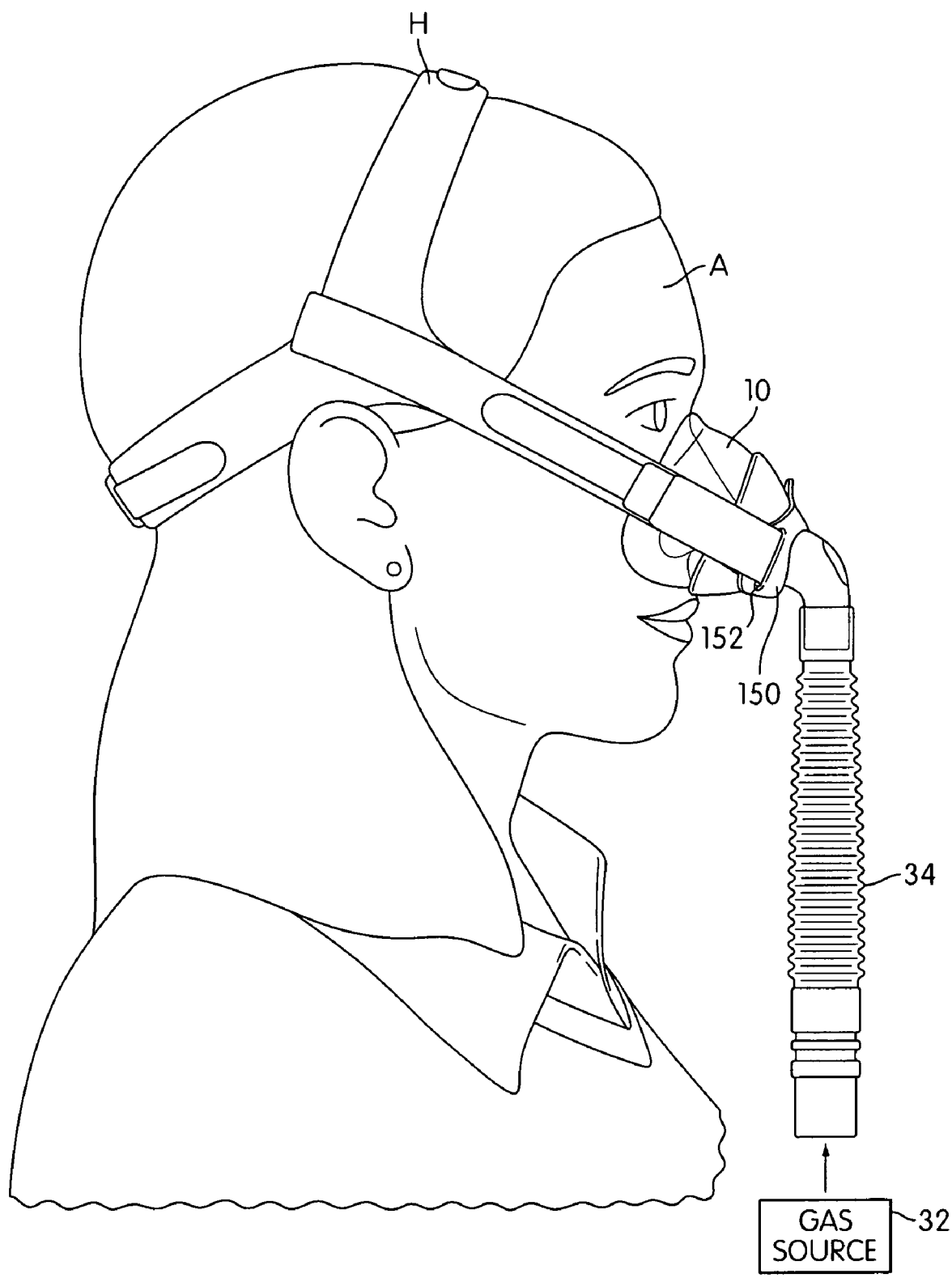
FIG. 1 is a left side perspective view of a patient interface assembly mounted operatively on the face of a patient in accordance with an embodiment of the present invention.
Figure 2:
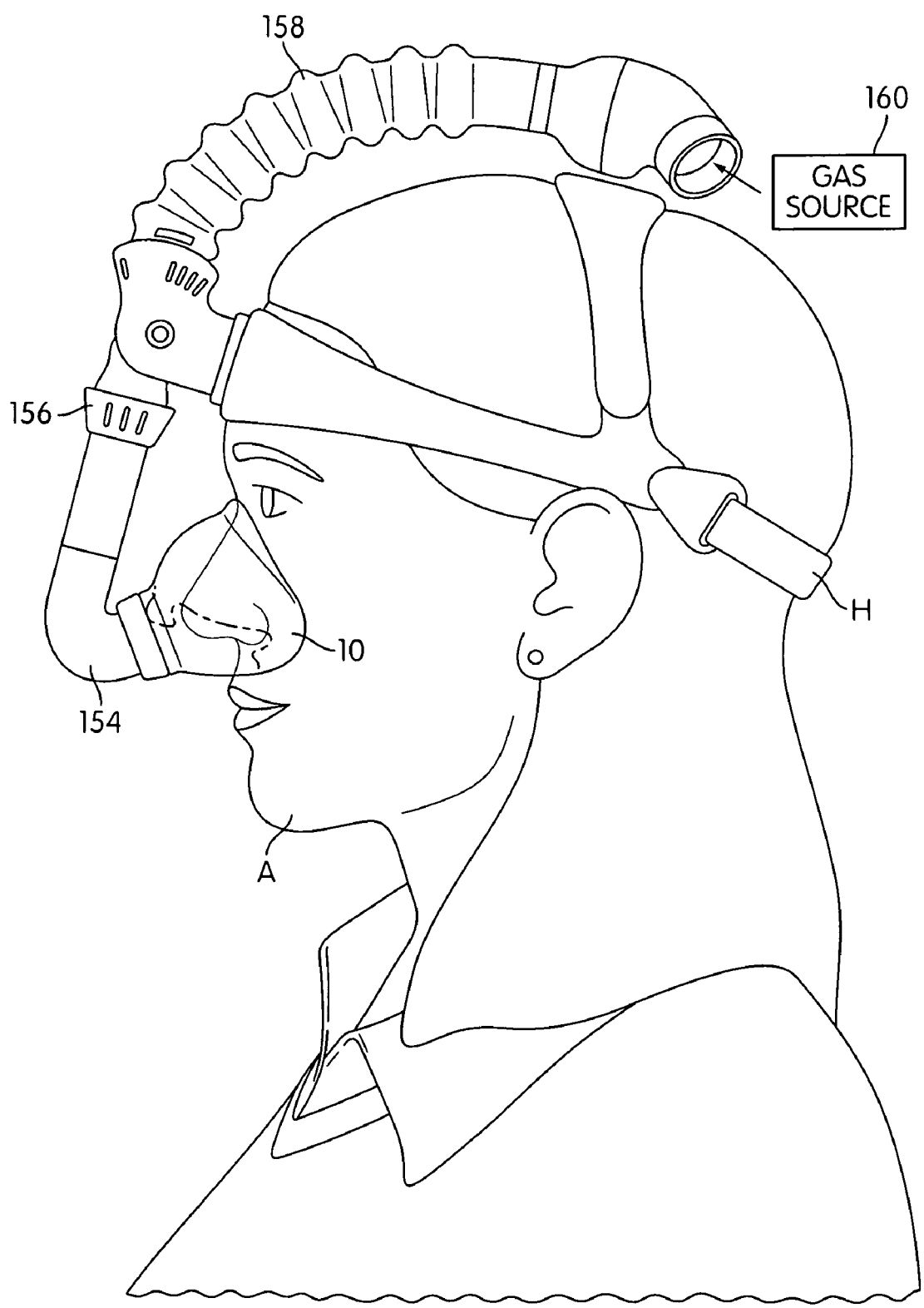
FIG. 2 is a right side perspective view of another patient interface assembly mounted operatively on the face of the patient in accordance with an embodiment of the present invention.
Figure 6:
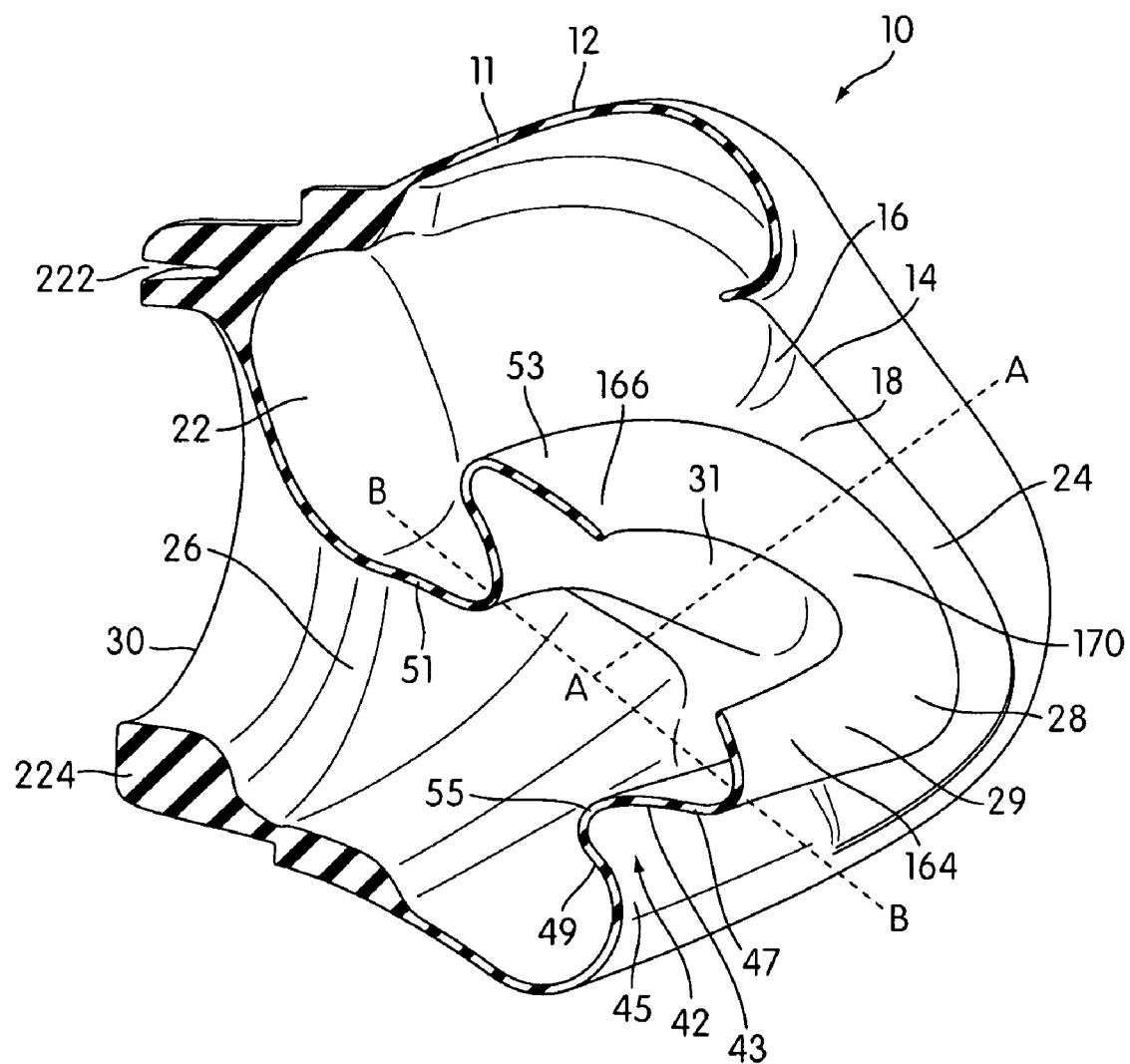
FIG. 6 is a cross-sectional view of the patient interface in accordance with an embodiment of the present invention.
Figure 7:
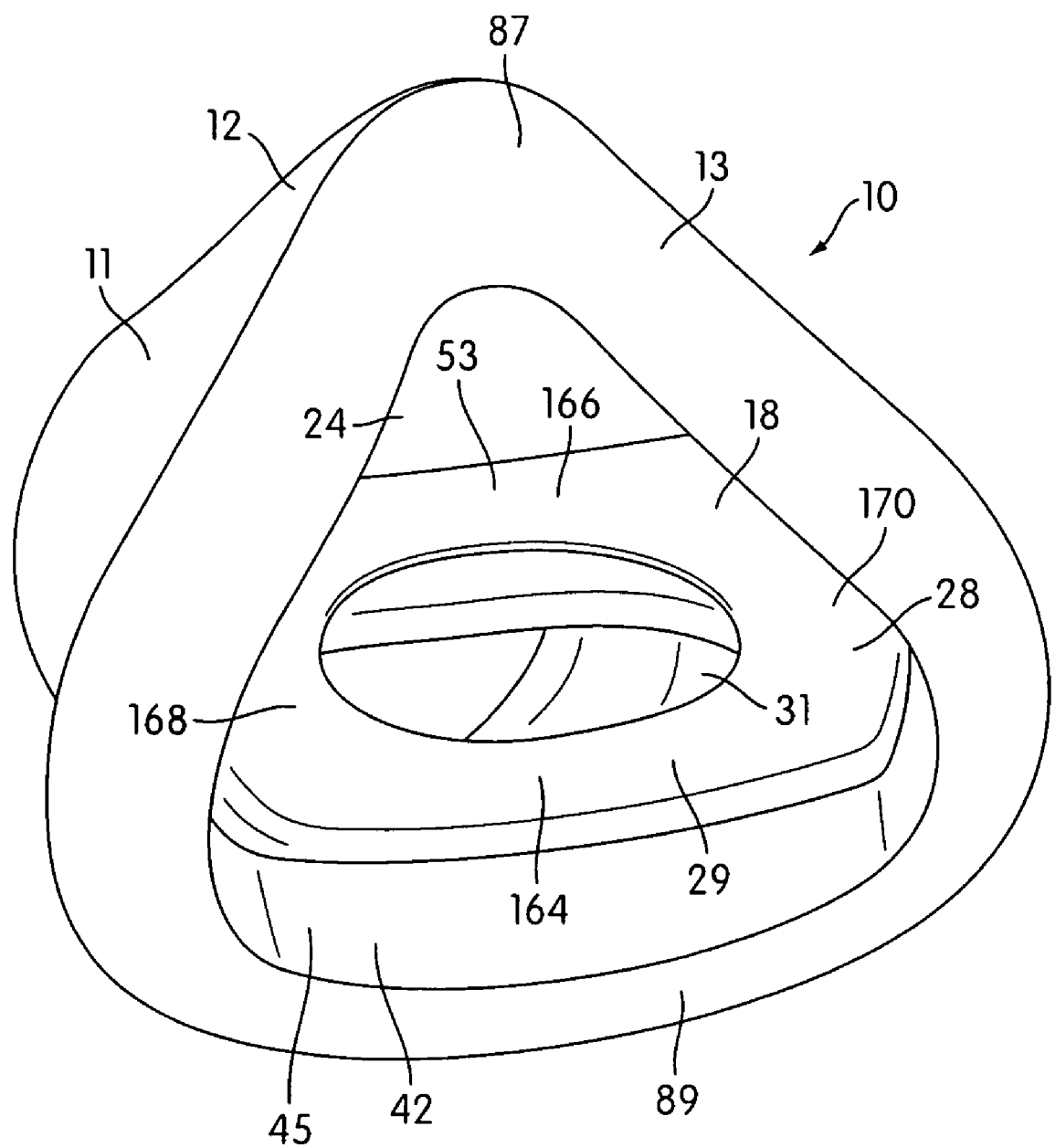
FIG. 7 is a perspective view of the patient interface in accordance with an embodiment of the present invention.
Figure 8:
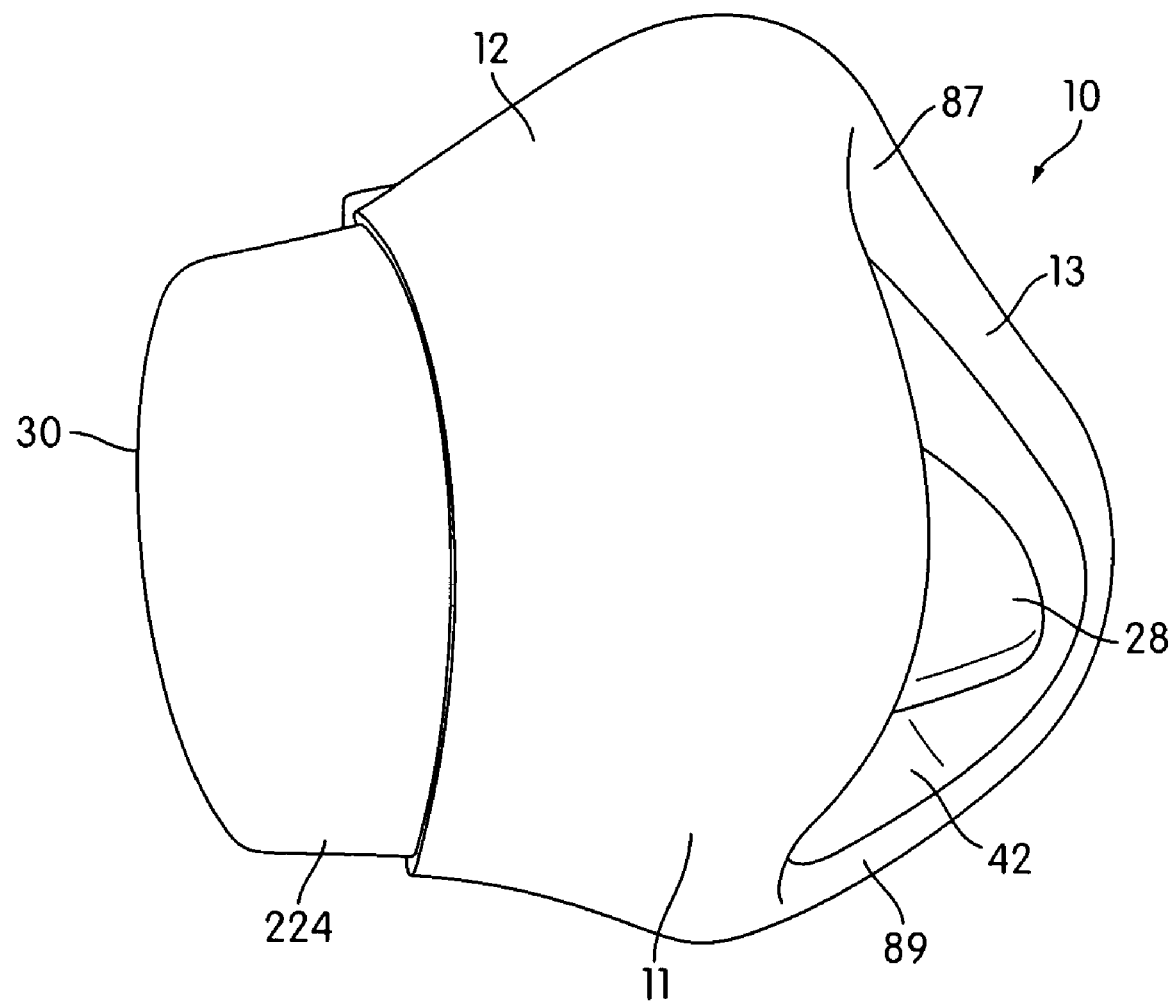
FIG. 8 is another left side perspective view of the patient interface in accordance with an embodiment of the present invention.
Figure 9:
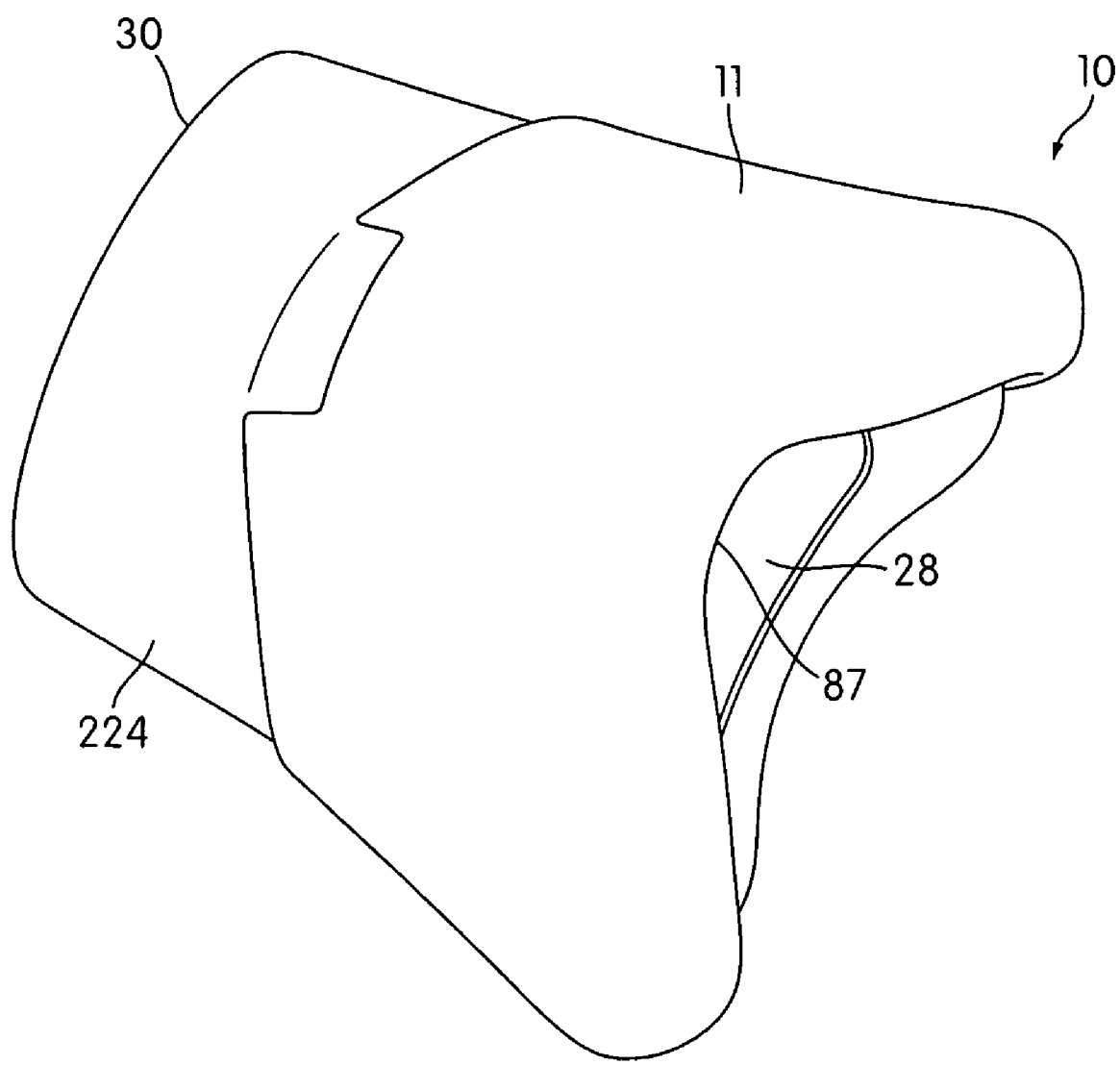
FIG. 9 is a top perspective view of the patient interface in accordance with an embodiment of the present invention.

The patient interface 10 includes a body member 11, a partition 22 (as shown in FIG. 6), a nasal seal portion 28, and a port 30. The partition 22 is integral with the body member 11, and separates an interior 18 of the body member 11 into a first chamber 24 configured to receive a nose of a patient and a second chamber 26. The nasal seal portion 28 is integral with the partition 22, and projects therefrom into the first chamber 24. The nasal seal portion 28 includes a seal surface 29 and a gas passage 31 therethrough. The seal surface 29 is configured to conform with a lower portion of the nose that is surrounding nasal passages of the patient, without entering the nasal passages of the patient, when the patient interface 10 is mounted operatively on the face of the The patient interface 10 described above can be mounted operatively on face A of the patient in any suitable manner as shown in FIGS. 1 and 2. For example, a suitable device for mounting the patient interface 10 operatively on the face A of a patient is disclosed in U.S. Pat. No. 6,651,663 to Barnett et al., which is incorporated herein by reference in its entirety.

Figure 3:
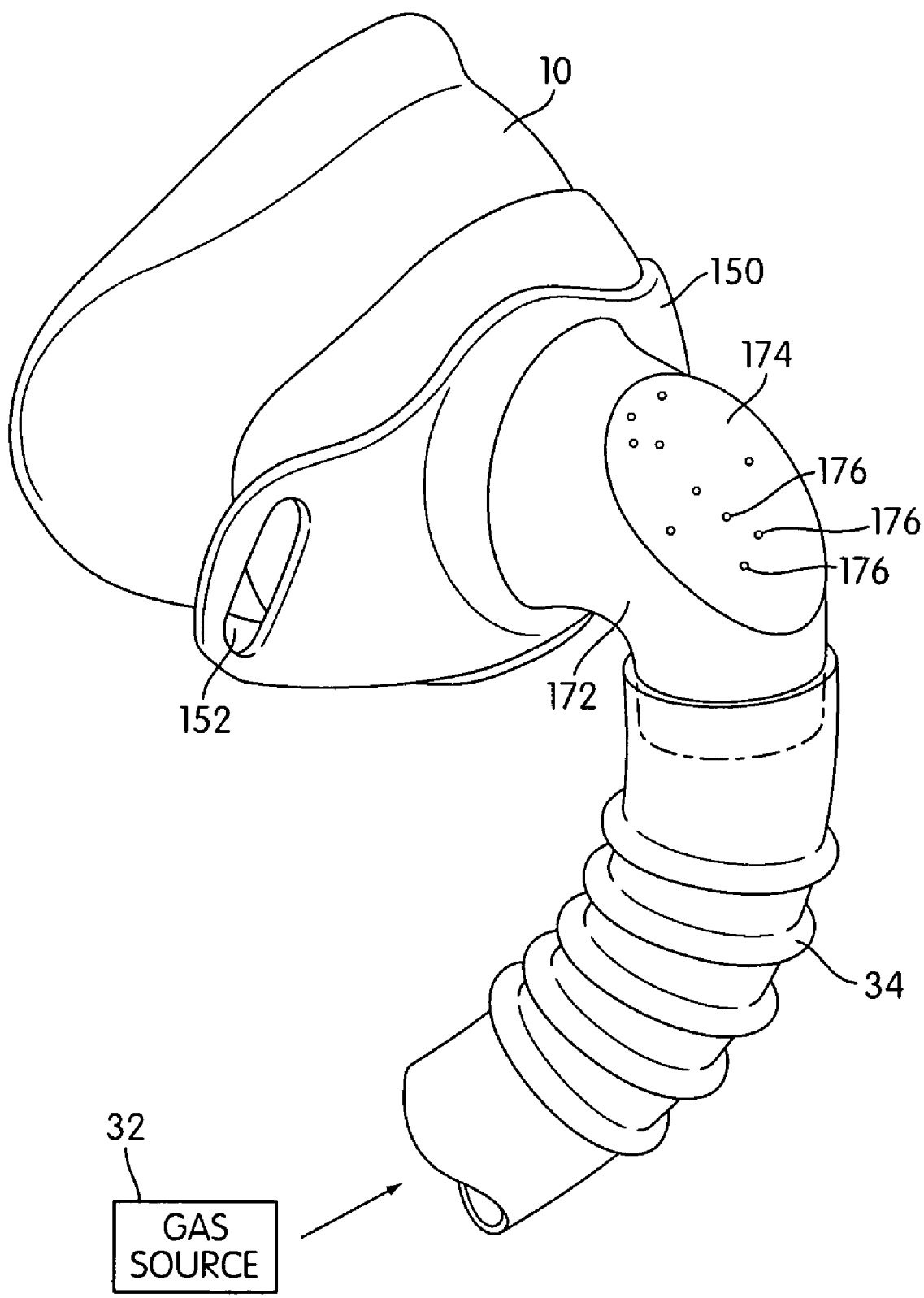
FIG. 3 is a left side perspective view of the patient interface assembly shown in FIG. 1, without a headgear, in accordance with an embodiment of the present invention.
Figure 10:
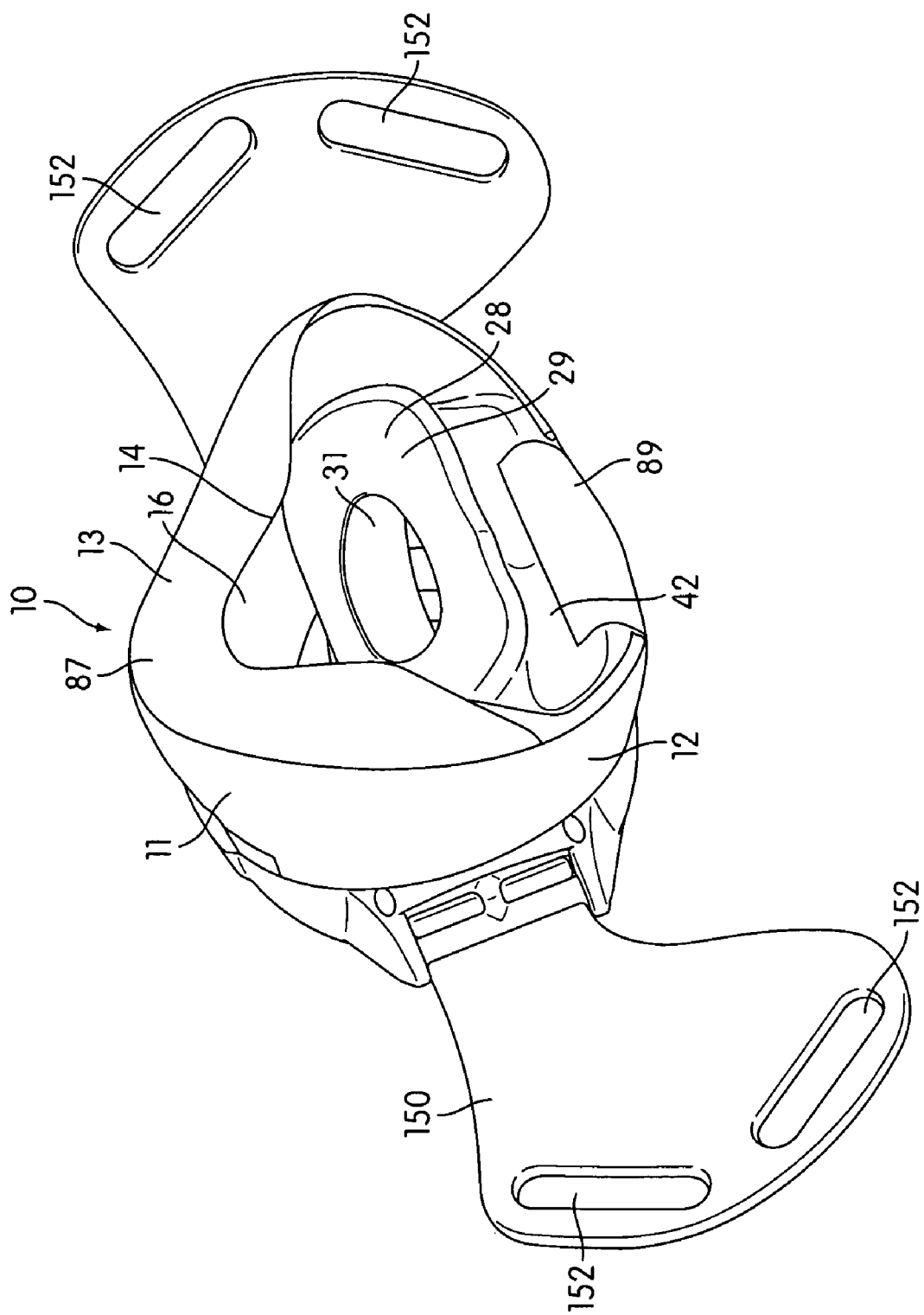
FIG. 10 is a front perspective view of the patient interface assembly in accordance with an embodiment of the present invention.
Figure 11:
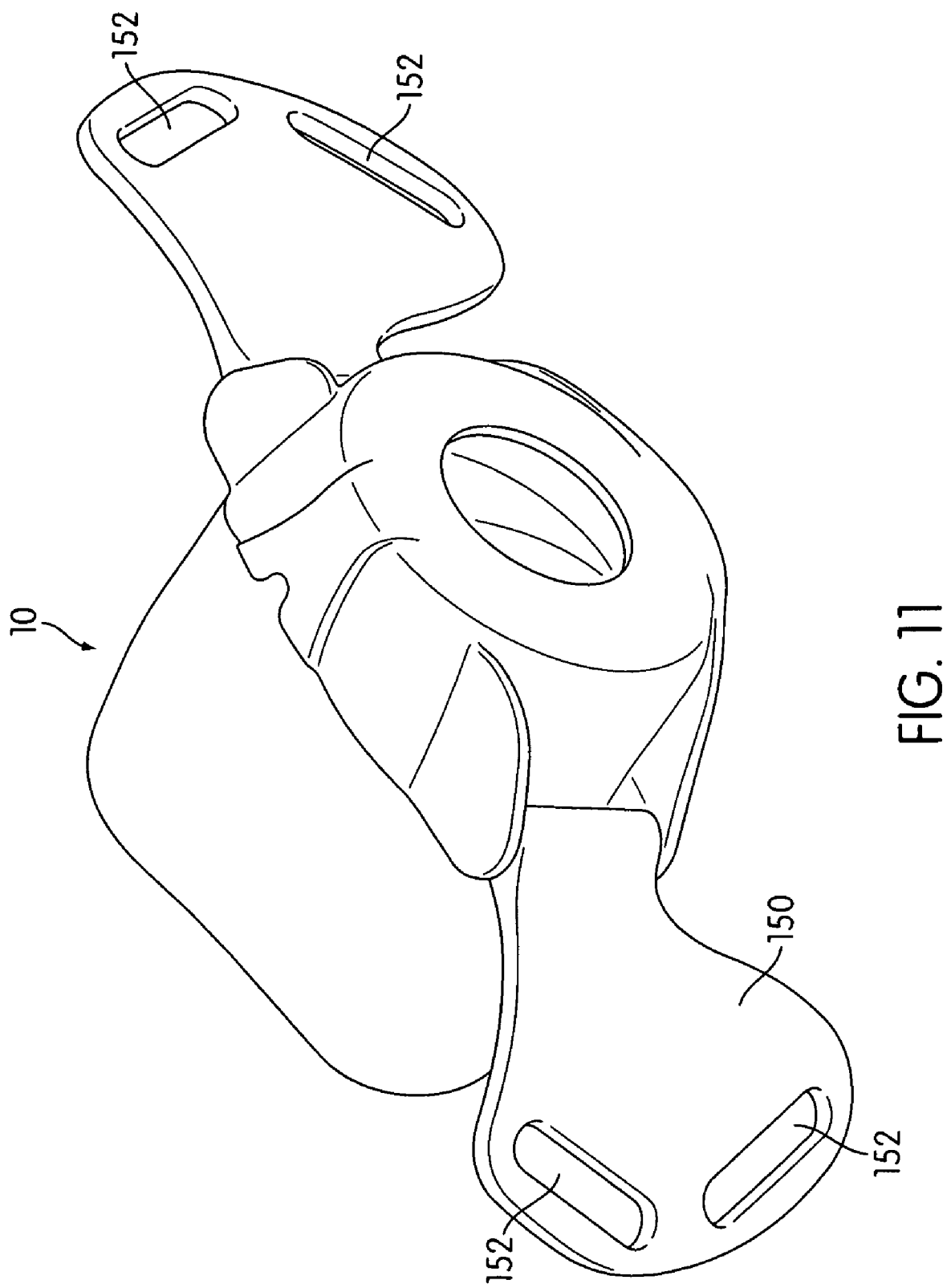
FIG. 11 is a rear perspective view of the patient interface assembly in accordance with an embodiment of the present invention.

As shown in FIGS. 1 and 3, a collar 150 can be mated with the patient interface 10. The collar 150 includes a plurality of cutouts 152 that function as headgear attachment points for securing a headgear H to the collar 150. In the illustrated embodiment, as shown in FIGS. 1 and 3, the collar 150 includes two cutouts 152 for headgear attachment points, each located on either side of the collar 150. However, this is not to be construed as limiting the invention since the number of headgear attachment points can be any desirable number, such as, without limitation, three or four. FIGS. 10 and 11 show the collar 150 having four cutouts 152 that function as headgear attachment points for securing the headgear H to the collar 150. The headgear H attached to the patient's head secures the patient interface assembly in position to enable the delivery of a suitable breathing gas to, and from, the patient via the gas passage 31 (as shown in FIGS. 4-9) in the nasal seal portion 28 (as shown in FIGS. 4-9). The gas can be provided to the patient via a gas source 32 and a gas delivery hose 34. In one embodiment, as shown in FIG. 3, the gas delivery hose 34 is connected to the collar 150 using an elbow or a conduit 172. In one embodiment, the elbow or the conduit 172 may be integral with the collar 150. In the illustrated embodiment, the elbow or conduit 172 may include an exhalation plate or surface 174 with a plurality of openings 176 therein. The plurality of openings 176 on the exhalation plate or surface 174 allow the exhaled gas to exit from the patient interface 10.

Another device for mounting the patient interface 10 operatively on the face A of a patient is disclosed in U.S. Patent Application Publication No. US 2005/0076913 to Ho et al., which is also incorporated herein by reference in its entirety. As shown in FIG. 2, the patient interface 10 can be mated with a shell 154, which in turn, is connected to a swivel 156 which, in turn, is coupled to an over-the-head hose 158 which is connected to a gas source 160. A headgear H attached to the crown of a patient's head secures the patient interface assembly in position to enable the delivery of a suitable breathing gas to, and from, the patient via the gas passage 31 (as shown in FIGS. 4-9) in the nasal seal portion 28 (as shown in FIGS. 4-9). Since various devices for attaching either embodiment of the patient interface 10 operatively on the face A of the patient are well known in the art, for purpose of simplicity, these devices, as well as any other devices for attaching the patient interface 10 operatively on the face A of the patient, will be denoted herein by the headgear H shown in FIGS. 1 and 2.

Figure 5:
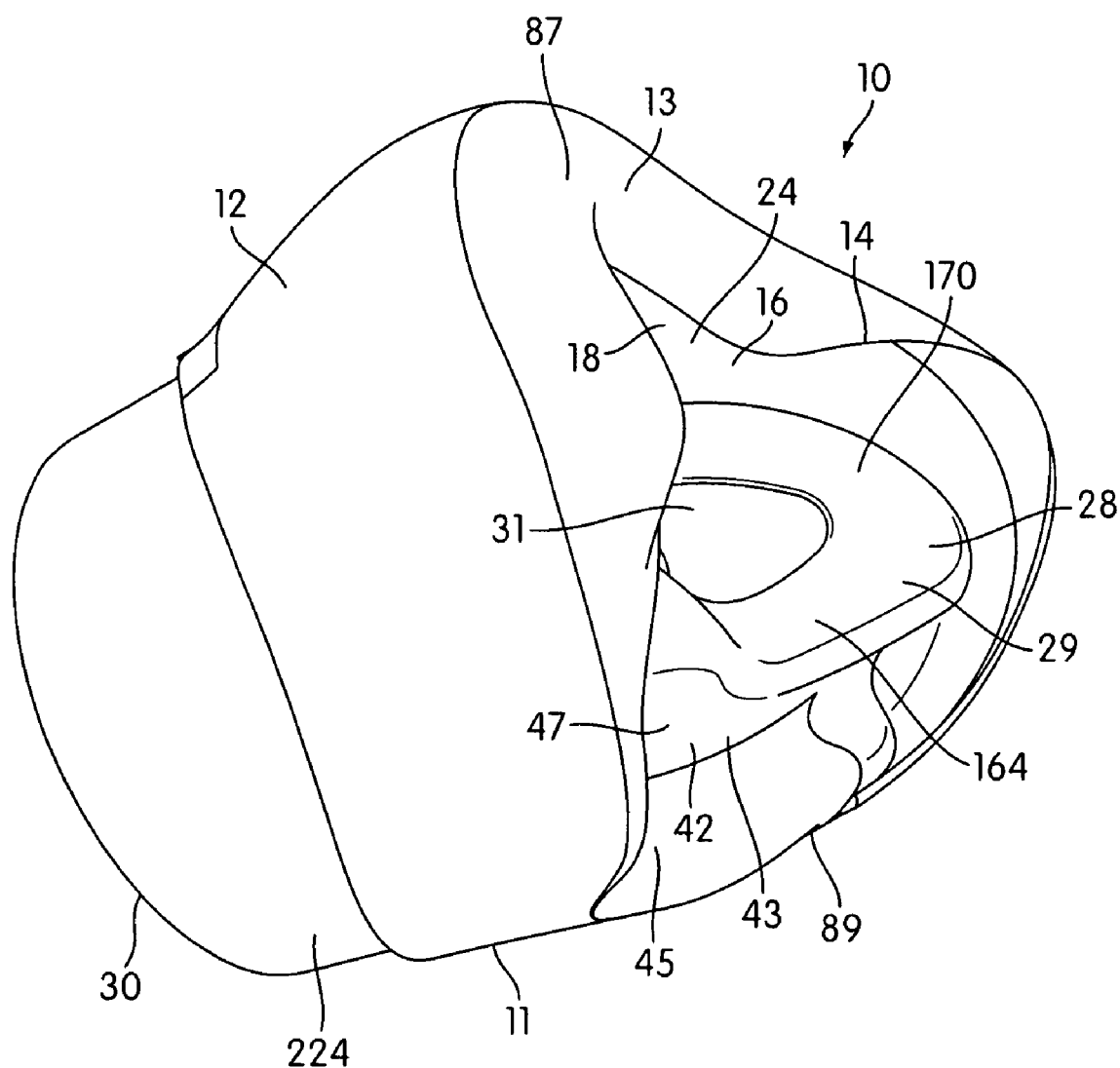
FIG. 5 is a left side perspective view of the patient interface in accordance with an embodiment of the present invention.
Figure 12:
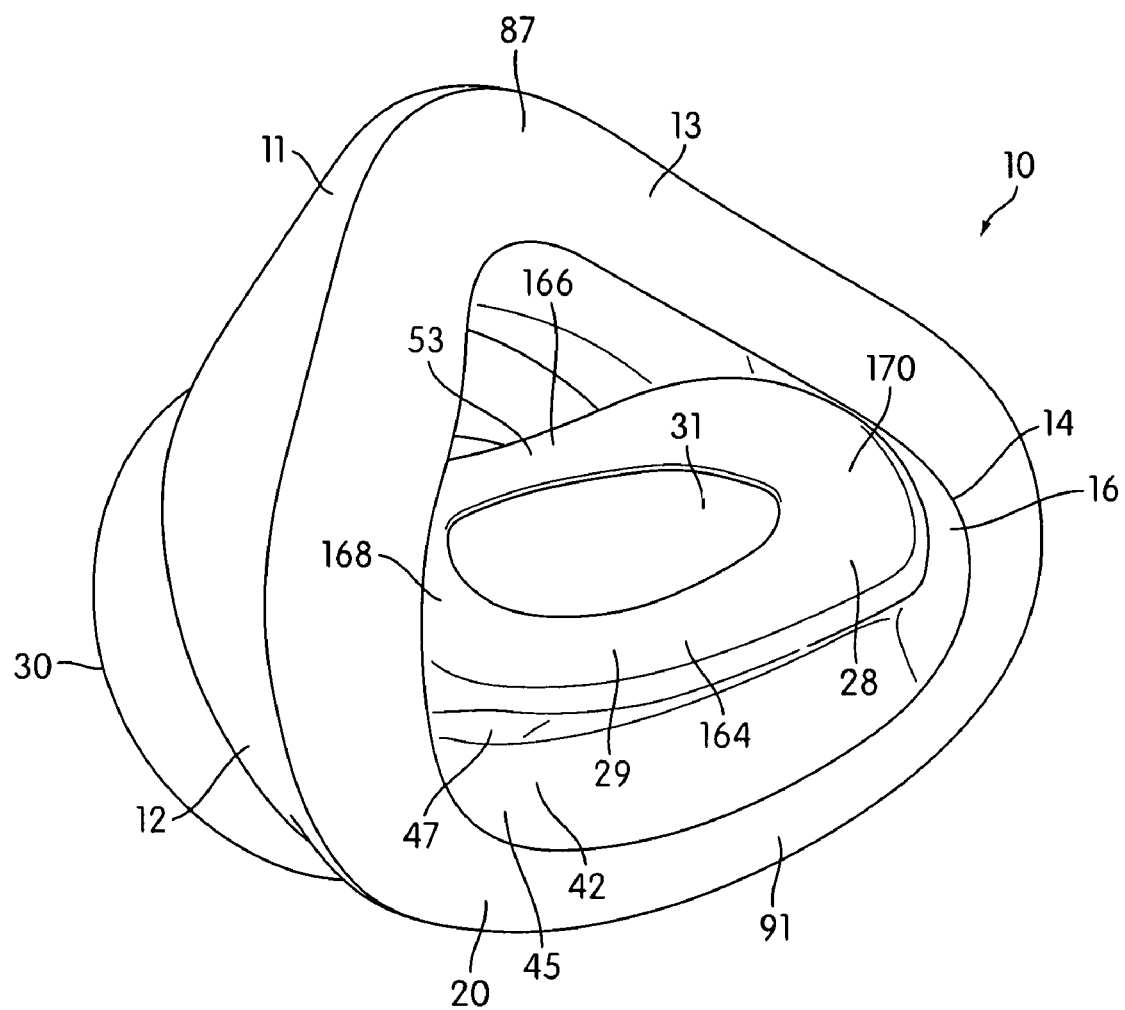
FIG. 12 is a perspective view of the patient interface in accordance with another embodiment of the present invention.
Figure 13:
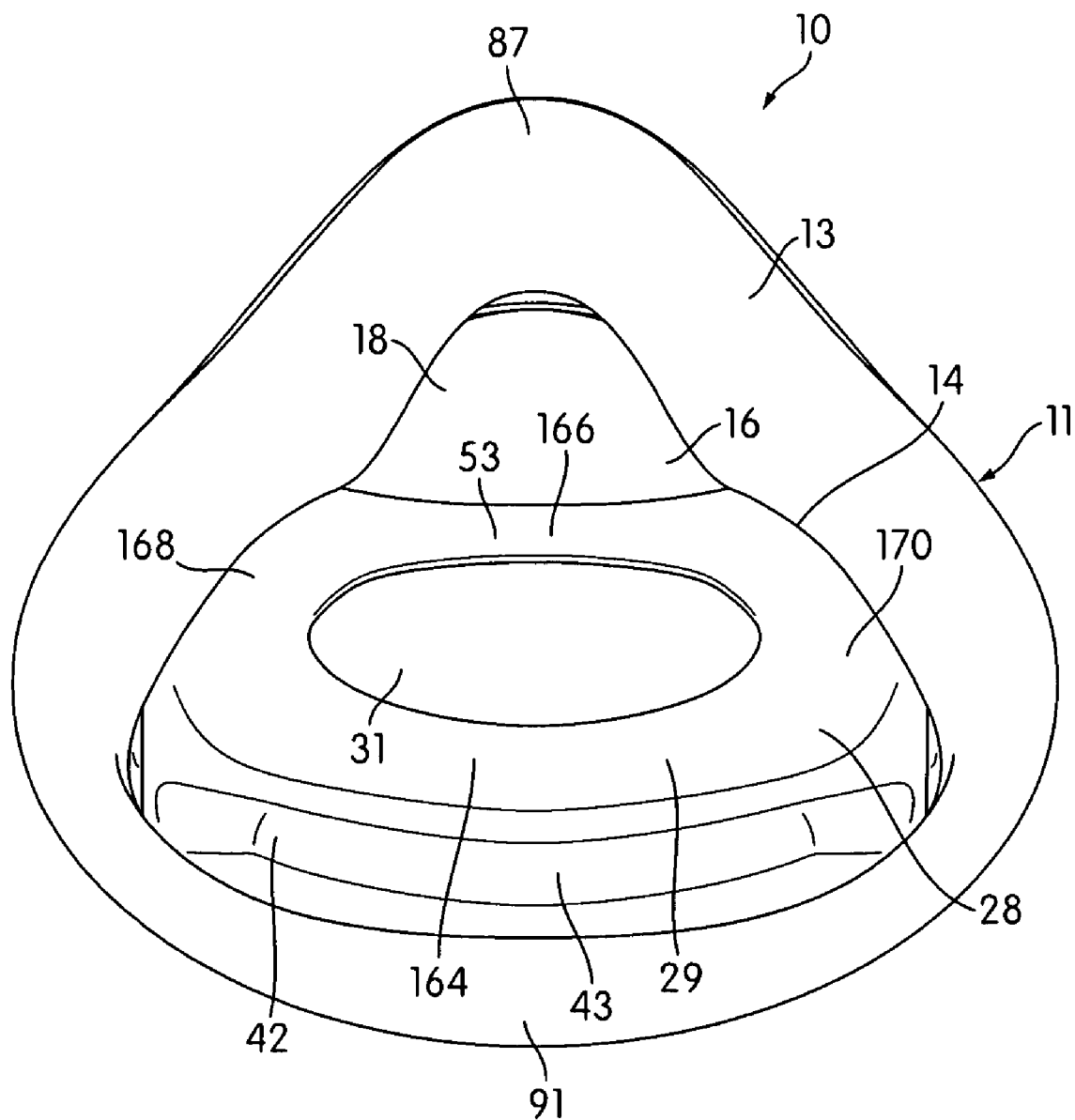
FIG. 13 is a front view of the patient interface in accordance with another embodiment of the present invention.
Figure 14:
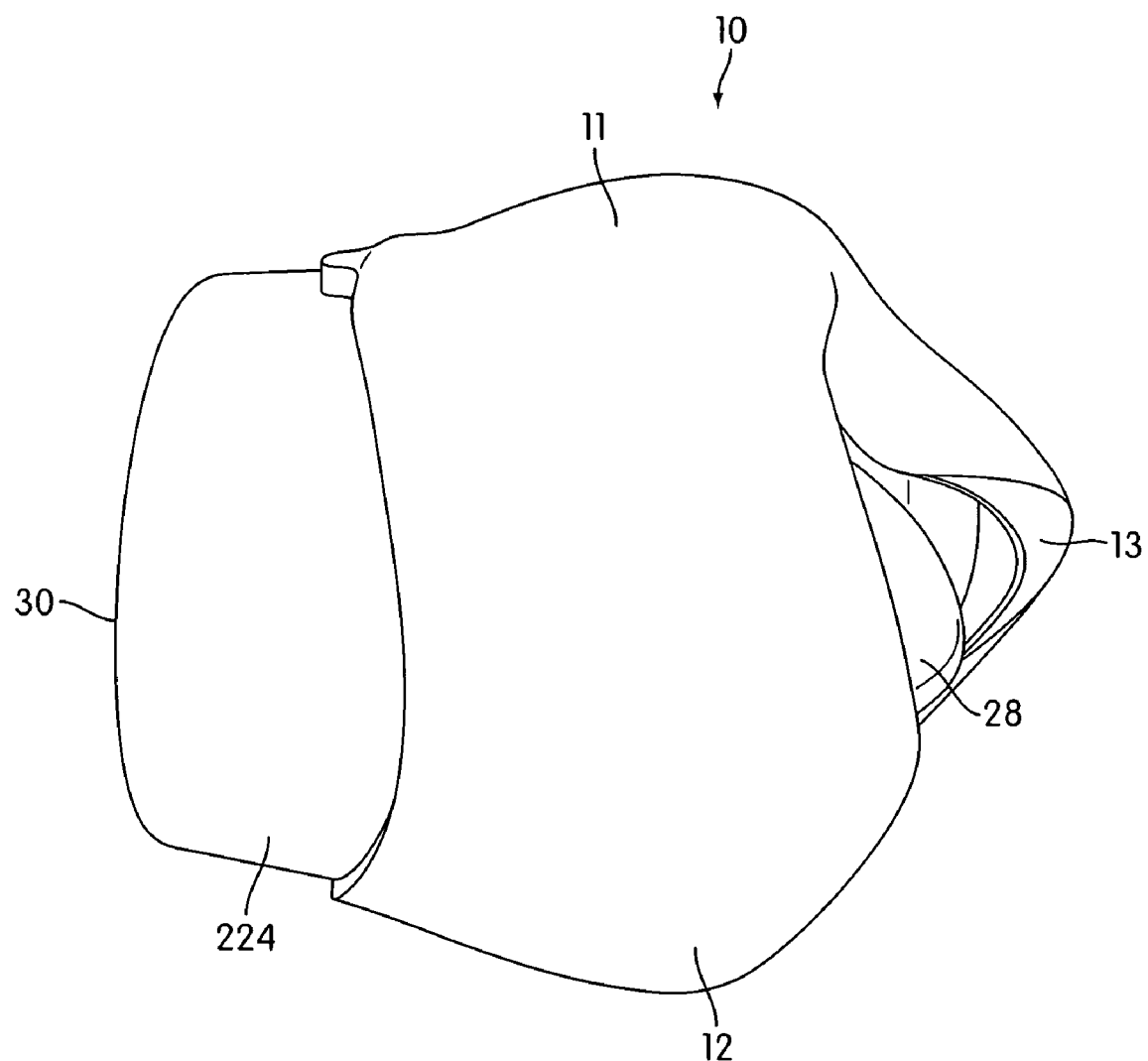
FIG. 14 is a left side perspective view of the patient interface in accordance with another embodiment of the present invention.

As seen in FIG. 5, the body member 11 includes a shell portion 12 and a cushion portion 13 with a peripheral edge 14 surrounding an opening 16 into an interior 18 of patient interface 10. The cushion portion 13, in the illustrated embodiment, rolls or curves inwardly towards the first chamber 24 to form a tight seal with the face of the patient, when the patient interface 10 is mounted operatively on the face of the patient. As will be discussed below, in another embodiment, as shown in FIG. 12-14, the cushion portion 13 may extend entirely along the peripheral edge 14 surrounding the opening 16 to provide more support.

In one embodiment, the cushion portion 13 of the body member 11 is sized such that an uppermost portion 87 of the cushion portion 13 overlies the nose of the patient, and a lowermost portion 89 of the shell portion 12, as is the case with the patient interface 10 shown in FIGS. 4-9, or a lower portion 91 of the cushion portion 13, as is the case with the patient interface 10 shown in FIGS. 12-14, overlies area of the patient above an upper lip and below the nose of the patient, responsive to the patient interface 10 being donned by the patient.

In one embodiment, the cushion portion 13 is a unitary piece of elastomeric material that is relatively flexible when a deformation force is applied thereto, yet returns to its original shape when the deformation force is removed. An example of a suitable material may include silicone material. In one embodiment, the cushion portion 13 is made of one or more elastomeric materials such as one or more materials selected from silicone material, thermoplastic elastomeric materials (i.e. polyurethane material, vinyl material, Ethylene-Propylene-Diene Rubber material, Styrene-Butadiene Rubber material, etc).

In one embodiment, when the patient interface 10 is made from a single elastomeric material, the patient interface 10 can be constructed and arranged to achieve different degrees of "stiffness" or "feel" by having different wall thicknesses in different areas. For example, the uppermost portion 87 (e.g., the portion that overlies the nose of the patient) of the cushion portion 13 includes a thinner section that provides a soft feel to conform with the facial contour of the user, while the body member 11 may include a substantially thicker section to provide a stiffer structure. In one embodiment, various portions of the patient interface 10 include specific wall thicknesses corresponding to their functions.

In one embodiment, the patient interface 10 is formed from various elastomeric materials having different properties, such as, hardness through co-injection of multiple casting. For example, a common method is co-inject the cushion in two to three silicone rubber materials with different hardness.

Figure 15:
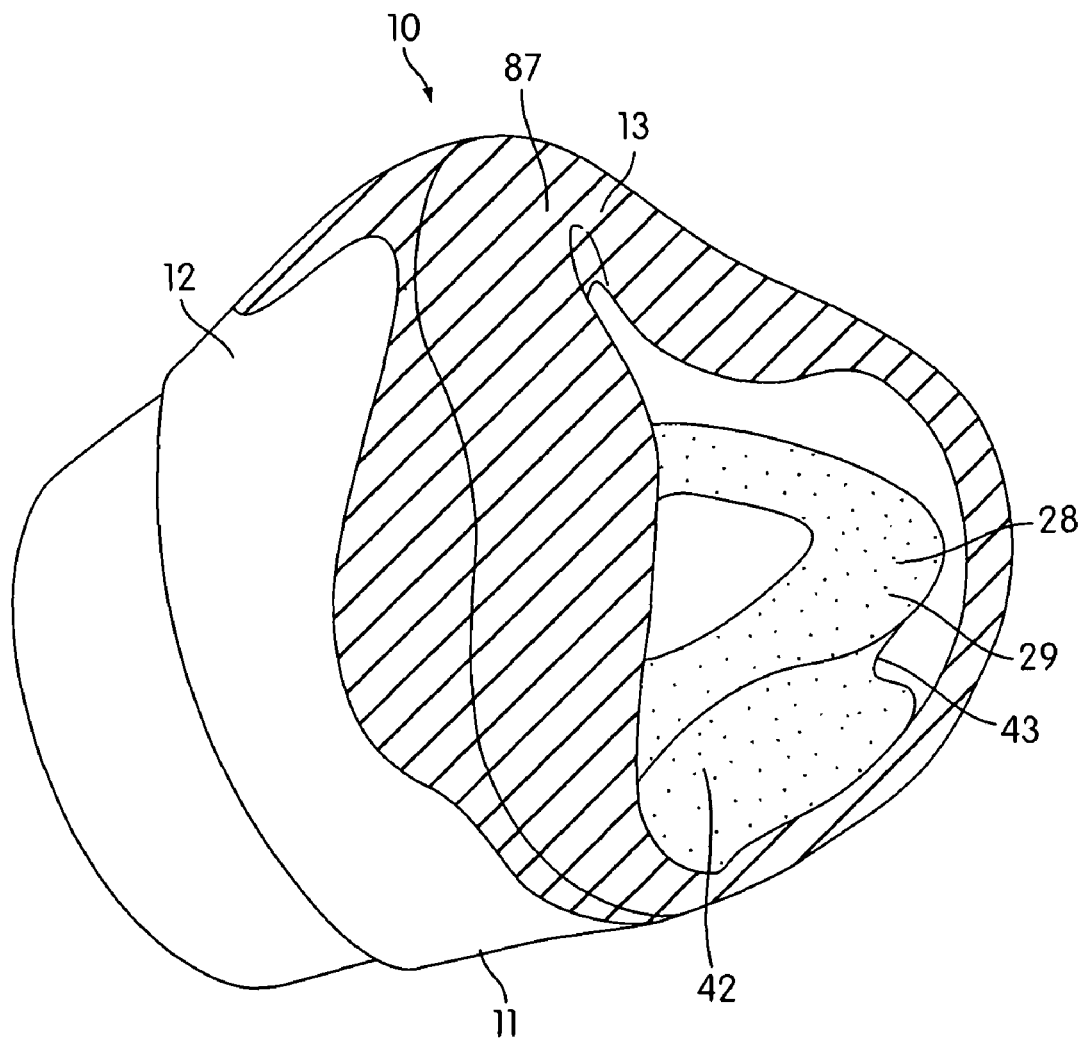
FIG. 15 is a perspective view of the patient interface formed from various elastomeric materials having different properties in accordance with an embodiment of the present invention.
Figure 15:
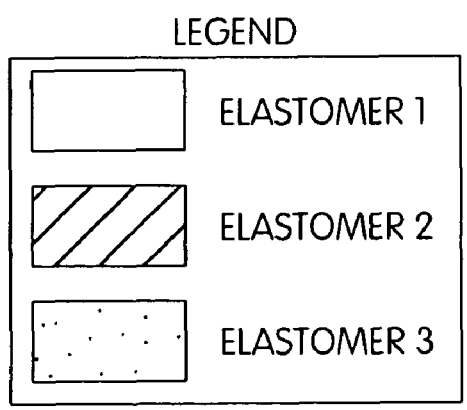

FIG. 15 shows a perspective view of the patient interface formed from different elastomeric materials having different properties in accordance with an embodiment of the present invention. In the illustrated embodiment, the patient interface 10 is formed from three different elastomeric materials having different hardnesses. In the illustrated embodiment, the shell portion 12 and/or the partition 22 (as shown in FIG. 6) are made of a first elastomeric material. In one embodiment, the first elastomeric material is in a range of Shore hardness from 60 to 80 Shore A. Alternatively, in another embodiment, the shell portion 12 is made of a second elastomeric material as mentioned below. In one embodiment, the cushion portion 13, the uppermost portion 87 of the cushion portion 13 that overlies the nose of the patient, the body member 11, and/or the shell portion 12 can be made of the second elastomeric material. In one embodiment, the second elastomeric material is in a range of Shore hardness from 30 to 40 Shore A. In one embodiment, the nasal seal portion 28, the seal surface 29, a flexible connection 42, and/or a bellows configuration 43 can be made of a third elastomeric material. In one embodiment, the third elastomeric material is the softest and is in a range of Shore hardness from 10 to 20 Shore A. This configuration of the patient interface 10 where the patient interface 10 is made of different elastomeric materials having different properties, such as hardness, provides a patient interface with relatively uniform wall thickness, thus, The opening 16 of the cushion portion 13 may be teardrop-shaped to accommodate the nose of the patient therein. One of ordinary skill in the art can best appreciate that the opening 16 of the cushion portion 13 may have a variety of other shapes without departing from the scope of the present invention including but not limited to generally triangular, generally pear shaped, and the like.

As shown best in FIG. 6, the partition 22 slopes from a position above the port 30 to a position adjacent a bottom of the opening 16. In one embodiment, other than the gas passage 31 in the nasal seal portion 28, the partition 22 forms a substantially gas tight seal between the first chamber 24 and the second chamber 26, whereupon the exclusive path for the passage of gas therebetween is via the gas passage 31 in the nasal seal portion 28.

Figure 4:
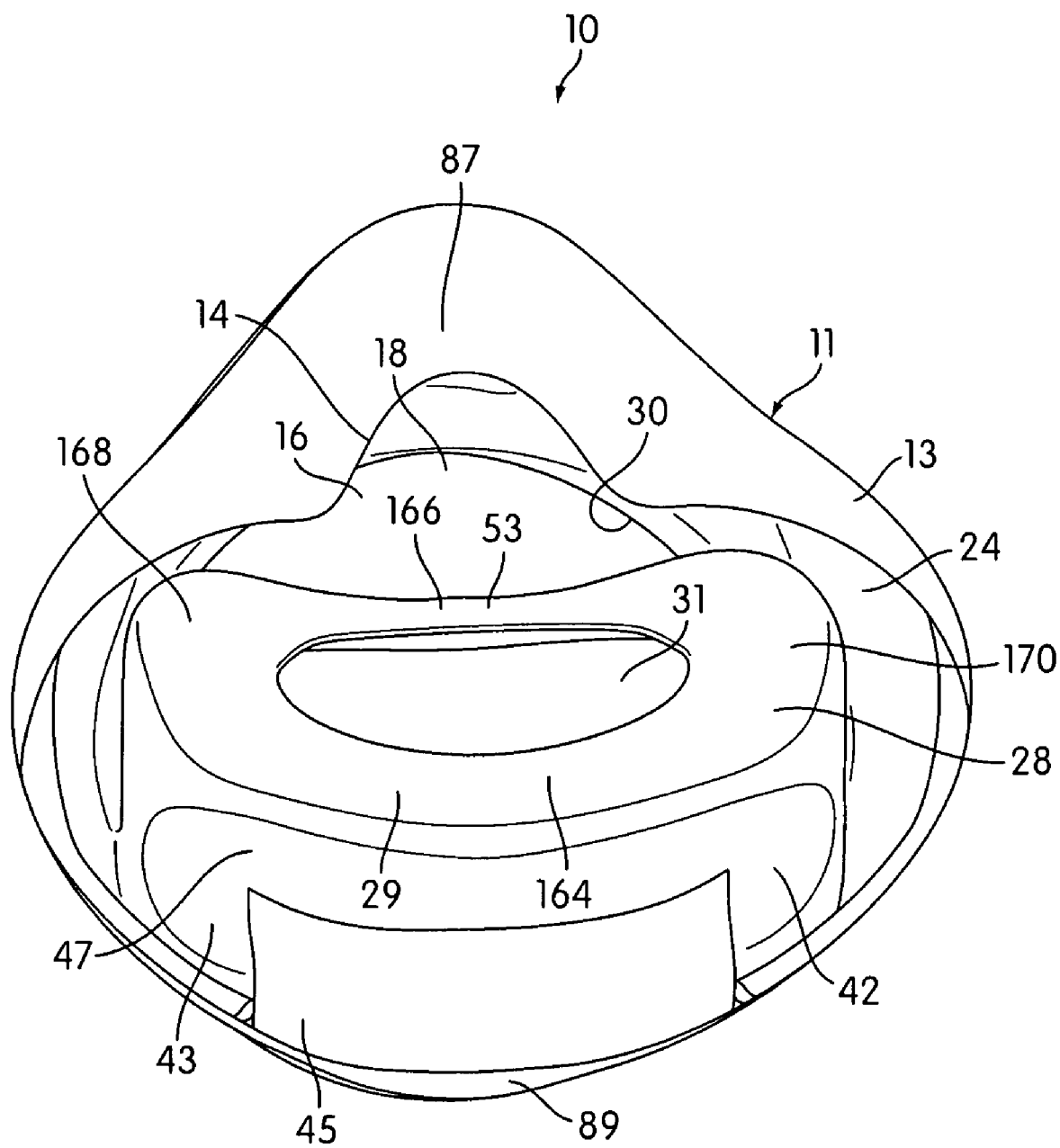
FIG. 4 is a front view of a patient interface in accordance with an embodiment of the present invention.

In one embodiment, the seal surface 29 of the nasal seal portion 28 is configured to conform with the lower portion of the nose that is surrounding nasal passages of the patient, without engaging with a central portion in the lower portion of the nose that separates the nasal passages of the patient. As shown in FIGS. 4 and 12, the seal surface 29 of the nasal seal portion 28 generally includes a pair of opposing, concave surfaces 164 and 166. The surface 166 is disposed for engaging the forwardmost lower surface of the patient's nose (in front of the nostrils), while the surface 164 is disposed for engaging the rearwardmost lower surface of the patient's nose (behind the nostrils). The surfaces 164, 166 are concave as they run laterally (left to right or viceversa). The surfaces 164 and 166 are separated by the gas passage 31 and are connected to one another on opposite sides thereof by side surface 168 and 170. The surfaces 168 and 170 are disposed to engage the lower left surface and lower right surface of the nose respectively (on opposite sides of the nostrils). The pair of opposing, concave surfaces 164 and 166, and the pair of opposing, side surfaces 168 and 170 are configured to conform with the contours of the lower portion of the nose that is surrounding nasal passages of the patient.

As noted above, the gas is delivered to and from the patient via the gas passage 31 in the nasal seal portion 28. In one embodiment, the gas passage 31 of the nasal seal portion 28 may be a teardrop-shaped. One of ordinary skill in the art can appreciate that the gas passage 31 of the nasal seal portion 28 may have a variety of other shapes without departing from the scope of the present invention including but not limited to generally triangular, generally rectangular, generally pear shaped, generally elliptical, and the like.

As shown best in FIG. 6, the port 30 comprises a thicker portion of material 224 (i.e., the port 30 has a thickened configuration) in comparison with the outer seal or the cushion portion 13 to make the port 30 more rigid thereby facilitating creation of a gas tight seal with the elbow or a conduit 172 (as shown in FIG. 3). In one embodiment, the port 30 may include grooves 222 that facilitate insertion of the elbow or a conduit 172 (as shown in FIG. 3) into the patient interface 10.

In one embodiment, the patient interface 10 may include the flexible connection 42 between the nasal seal portion 28 and the partition 22. The flexible connection 42 is configured to adjust or alter an axial position and/or a pivotal position of the nasal seal portion 28 relative to the partition 22 to accommodate the nose so as to maintain a sealing contact between the nasal seal portion 28 and the lower portion of the nose. The flexible connection 42 moveably couples the nasal seal portion 28 to the partition 22.

In one embodiment, the flexible connection 42 comprises the bellows configuration 43. In another embodiment, the flexible connection 42 may have an accordion design. It is contemplated, however, various other configurations for the flexible connection 42 could be used without departing from the scope of the present invention. In one embodiment, the flexible connection 42 includes a peripheral (or partially peripheral), inwardly extending portion 47 which extends inwardly as it extends downwards away from the seal surface 28, to form a narrowed diameter portion 55 of material that facilitates pivotal and axial movement of the seal surface 28. As the connection 42 continues to extend away from the seal surface 28, it transitions from the narrowed diameter portion 55 to an outwardly extending portion 45 (as shown in FIG. 6). The outwardly extending portion 45 extends outwardly as it extends downwards away from the narrowed diameter portion 55, to form a rounded portion of material that transitions into the shell portion 12 or the cushion portion 13 of the patient interface 10. In one embodiment, the flexible connection 42 is in the form of an axially flexible connection that facilitates desirable axial positioning of the seal surface 29 of the nasal seal portion 28 along the axial direction of the gas passage 31. In other words, the axially flexible connection is configured to adjust an axial position of the nasal seal portion 28 towards or away from to the partition 22 (or enlarged portion 45) to accommodate the size of the nose so as to maintain a sealing contact between the nasal seal portion 28 and the lower portion of the nose, when patient interface 10 is mounted operatively on the face A of the patient. The axial movement of seal portion 28 is facilitated by the shape, material, and configuration of the flexible connection 42.

The flexible connection 42 is also constructed and arranged to facilitate desirable pivotal positioning of the seal surface 29 of the nasal seal portion 28 along a lateral direction A-A (as shown in FIG. 6), as well as the fore-aft direction B-B, relative to the partition 22. In other words, the pivotally flexible connection is shaped, configured and made from material that facilitates a pivotal adjustment of the position of the nasal seal portion 28 relative to the partition 22 to accommodate the nose so as to maintain a sealing contact between the nasal seal portion 28 and the lower portion of the nose, when patient interface 10 is mounted operatively on the face A of the patient. In one embodiment, the focal point of the flexing action that facilitates pivoting and/or axial compression action takes place largely at the narrowed diameter portion 55.

When a flow of gas is supplied from the pressure support system (not shown) to the patient interface 10, the gas enters the second chamber 26 of the patient interface via the port 30 of the patient interface 10. The pressure of the gas in the second chamber 26 of the patient interface 10 engages under the seal surface 29 of the nasal seal portion 28 to push the flexible connection 42 upwardly in the axial direction away from the partition 22 and into forcible contact with the lower surface of patient's nose.

Specifically, as shown in FIG. 6, in the case of the axially flexible connection, as the gas enters the second chamber 26 of the patient interface 10 via the port 30 of the patient interface 10, the pressure of the gas in the second chamber 26 of the patient interface 10 engages with surfaces 49 and 51 of the axially flexible connection 42. The pressure of the gas in the second chamber 26 of the patient interface 10 forces up the axially flexible connection 42. This action of the axially flexible connection 42 therefore urges the seal surface 29 away from the partition 22, towards the nose of the patient so as to maintain a sealing contact between the nasal seal portion 28 and the lower portion of the nose, when patient interface 10 is mounted operatively on the face A of the patient. Also, when patient interface 10 is mounted operatively on the face A of the patient, the lower portion of the nose engages with an end portion 53 of the seal surface 31 of the nasal seal portion 28 to push the seal surface 31 of the nasal seal portion 28 downwardly in the axial direction (relative to the gas flow axis of the gas passage 31) towards the partition 22. The spring action generated by the elasticity of the material of the axially flexible connection 42 applies a sealing force to the lower surface of the nose, thus, maintaining a sealing contact between the seal surface 29 of the nasal seal portion 28 and the lower portion of the nose when patient interface 10 is mounted operatively on the face A of the patient.

Additional sealing force is applied when pressure is provided to the patient interface 10 via the port 30, by pressure being received by the underside of the seal portion 28 to force surface 29 into the nose. The action of the pivotally flexible connection 42 moves the seal surface 29 of the nasal seal portion 28 laterally (left and right) and in the fore-aft direction relative to the partition 22 so as to maintain a sealing contact between the nasal seal portion 28 and the lower portion of the nose, when patient interface 10 is mounted operatively on the face A of the patient.

With reference to FIGS. 12-14 and with continuing reference to all previous figures, in an alternate embodiment of the patient interface 10, the cushion portion 13 that rolls or curves inwardly into the first chamber 24 extends along the entire peripheral edge 14 surrounding the opening 16 so as to provide more support, when the patient interface 10 is mounted operatively on the face of the patient. In this embodiment, the rolled cushion portion 13 engages not only the bridge of the nose, but also engages the skin on the patients face above the upper lip (and face surfaces between the bridge of the nose and above the upper lip) to create a peripheral seal around the nose. This is in contrast to the embodiment of the patient interface 10 shown in FIGS. 4-11, wherein the rolled cushion portion 13 extends partially along the peripheral edge 14 and is employed mainly to engage only the bridge of the patients nose, rather than to encircle the nose. Other than the rolled cushion portion 13 extending partially along the peripheral edge 14 in FIGS. 4-11 and the rolled cushion portion 13 extending entirely along the peripheral edge 14 in FIGS. 12-14, the embodiment of the patient interface 10 shown in FIGS. 12-14 is similar to the embodiment of the patient interface 10 shown in FIGS. 4-11. Accordingly, additional detailed description of the embodiment of the patient interface 10 shown in FIGS. 12-14 will not be included herein to avoid unnecessary redundancy.

As can be seen, the patient interface 10 provides a one-piece or unitary patient interface for use by a patient. The patient interface can be formed by any suitable process for forming a unitary structure such as injection molding, rotational molding, blow molding, etc. The patient interface 10 is generally made from a suitable biocompatible material that is resilient upon completion of the manufacturing process. In one embodiment, the rolled cushion portion 13 and/or the nasal seal portion 28 of each embodiment of the patient interface 10 discussed above are more resilient than the remaining portions of the unitary structure for patient comfort and to facilitate forming suitable good seal(s) with the face and/or the lower portion of the nose that is surrounding the nasal passages of the patient when in use to prevent substantial gas leakage.

The patient interface 10 includes both the cushion portion 13 that fits about the patient's nose (over the bridge of the nose and beneath the nose, against the skin above the upper lip) as well as the seal surface 29 of the nasal seal portion 28 that conforms with the lower portion of the nose that is surrounding the nasal passages of the patient. This configuration separates the function of stabilizing the patient interface from the function of creating a seal between the patient and the patient interface 10. In one embodiment, the cushion portion 13 of the patient interface 10 operates to stabilize and secure the patient interface 10 in place and has a generally pyramidal-shape. In the event that forces are exerted longitudinally along an axis through port 30 towards the face A of the patient, the rolled cushion portion 13 will bear a majority of the applied forces rather than the seal surface 29 of the nasal seal portion 28.

The region about the nares or nasal passages of a patient are well-known to be particularly sensitive. Therefore, the resilient seal surface 29 is configured to conform with the lower portion of the nose surrounding nasal passages of the patient, without entering the nasal passages of the patient, when the patient interface 10 is mounted operatively on the face of the patient. In other words, the patient interface 10 of the present invention does not include any intrusive nasal pillows that are configured for even least partial insertion into the nostrils of the patient to maintain a seal between the patient and the patient interface. Thus, the non-intrusive patient interface of the present invention reduces discomfort to the patient. As noted above, the seal surface 29 of the nasal seal surface 28 is predominately responsible for maintaining a seal between the patient and the patient interface 10 sufficient to deliver gas to the patient.

In one embodiment, the patient interface 10 is formed from a unitary construction thus minimizing the potential for parts to be lost. For example, the nasal seal portion 28 are integrally formed with the partition 22. Alternatively, the nasal seal portion 28 may be formed separately from the partition 22 and adhered or otherwise joined to the patient interface 10. This would permit the patient to select a nasal seal portion that is specifically sized and shaped for the particular shape of the patient's nose, or be replaced should excessive wear occur. In either embodiment, the gas supplied to the patient is mixed in the second chamber 26 before being delivered to the patient via the gas passage 31 in the nasal seal portion 28. This intermixing ensures that the same gas is delivered at the same pressure to both nasal passages of the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface comprising:
    a body member;
    a partition integral with the body member, the partition separating an interior of the member into a first chamber configured to receive a nose of a patient and a second chamber;
    a nasal seal portion integral with the partition and projecting therefrom into the first chamber, the nasal seal portion having a seal surface and a gas passage therethrough, the seal surface configured to conform with a lower portion of the nose that is surrounding nasal passages of the patient, without entering the nasal passages of the patient, when the patient interface is mounted operatively on the face of the patient; and
    a port integral with the member in fluid communication with the second chamber for delivery of gas to the patient via the gas passage in the nasal seal portion.

2. The patient interface of claim 1, further comprising an axially flexible connection between the nasal seal portion and the partition, the axially flexible connection is configured to adjust an axial position of the nasal seal portion relative to the partition to accommodate the nose so as to maintain a sealing contact between the nasal seal portion and the lower portion of the nose.

3. The patient interface of claim 2, wherein the axially flexible connection comprises at least one bellows.

4. The patient interface of claim 2, wherein the axially flexible connection comprises an inwardly extending portion and an outwardly extending portion alternately formed along an axial direction of the patient interface.

5. The patient interface of claim 1, further comprising a pivotally flexible connection between the nasal seal portion and the partition, the pivotally flexible connection is configured to adjust a pivotal position of the nasal seal portion relative to the partition to accommodate the nose so as to maintain a sealing contact between the nasal seal portion and the lower portion of the nose.

6. The patient interface of claim 5, wherein the pivotally flexible connection comprises at least one bellows.

7. The patient interface of claim 5, wherein the pivotally flexible connection comprises an inwardly extending portion and an outwardly extending portion alternately formed along an axial direction of the patient interface.

8. The patient interface of claim 1, further comprising an axially and pivotally flexible connection between the nasal seal portion and the partition, the axially and pivotally flexible connection is configured to adjust an axial position and a pivotal position of the nasal seal portion relative to the partition to accommodate the nose so as to maintain a sealing contact between the nasal seal portion and the lower portion of the nose.

9. The patient interface of claim 8, wherein the axially and pivotally flexible connection comprises at least one bellows.

10. The patient interface of claim 8, wherein the axially and pivotally flexible connection comprises an inwardly extending portion and an outwardly extending portion alternately formed along an axial direction of the patient interface.

11. The patient interface of claim 1, wherein the member comprises a shell portion and a cushion portion, wherein the cushion portion is sized such that an uppermost portion of the cushion portion overlies the nose of the patient, and a lowermost portion of the cushion portion overlies area of the patient above an upper lip and below the nose of the patient, responsive to the patient interface being donned by the patient.

12. The patient interface of claim 11, wherein the cushion portion comprises a teardrop-shaped opening to accommodate the nose of the patient therein.

13. The patient interface of claim 11, wherein the cushion portion is configured to roll inwardly into the first chamber to form a tight seal with the face of the patient, when the patient interface is mounted operatively on the face of the patient.

14. The patient interface of claim 1, wherein the seal surface is configured to conform with the lower portion of the nose that is surrounding nasal passages of the patient, without engaging with a central portion in the lower portion of the nose that separates the nasal passages of the patient.

15. The patient interface of claim 1, wherein the seal surface comprises a generally concave surface to conform with the contours of the lower portion of the nose that is surrounding nasal passages of the patient.

16. A patient interface, comprising:
    an outer body member formed from a resilient material;
    a peripheral outer seal integral with the body member, the outer seal comprising peripheral surface regions arranged to engage the bridge of a patient's nose and a region above the patient's upper lip;
    a nasal seal portion at least partially disposed within the outer body member, the nasal seal portion having an upper seal surface and a gas passage therethrough, the upper seal surface having a generally concave configuration as it extends in a left-right direction and arranged to conform with a lower portion of the nose that surrounds that nasal passages of the patient, the upper seal surface being devoid of projections that would enter the nasal passages of the patient; and a port integral with the body member for delivering gas to the patient via the gas passage in the nasal seal portion.

17. The patient interface of claim 16, wherein the outer seal is configured to roll inwardly towards an interior of the outer body member to form a tight seal with the face of the patient, when the patient interface is mounted operatively on the face of the patient.

18. The patient interface of claim 16, further comprising a flexible connection between the nasal seal portion and the outer body member, the flexible connection is configured to adjust a position of the nasal seal portion relative to the outer body member to accommodate the nose so as to maintain a sealing contact between the nasal seal portion and the lower portion of the nose.

19. The patient interface of claim 18, wherein the flexible connection comprising a peripheral, inwardly extending portion which extends inwardly as it extends downwards away from the nasal seal surface, to form a narrowed diameter portion of material that facilitates pivotal and axial movement of the nasal seal surface.

20. The patient interface of claim 16, wherein the port is thicker than the outer seal thereby making the port rigid for creating a gas tight seal with a conduit.

21. The patient interface of claim 16, wherein the outer body member comprising a partition separating an interior of the member into a first chamber configured to receive a nose of a patient and a second chamber.

* * * * *